United States Patent [19]

Kuntz et al.

[11] 4,276,889
[45] Jul. 7, 1981

[54] URINE SPECIMEN COLLECTING DEVICE

[75] Inventors: David H. Kuntz, Los Angeles; James A. Ingram, Costa Mesa, both of Calif.

[73] Assignee: SHS Enterprises, Ltd., Newport Beach, Calif.

[21] Appl. No.: 60,217

[22] Filed: Jul. 24, 1979

Related U.S. Application Data

[63] Continuation-in-part of Ser. No. 31,427, Apr. 19, 1979.

[51] Int. Cl.³ ............................................. A61B 10/00
[52] U.S. Cl. ..................................... 128/761; 4/301
[58] Field of Search ................. 4/144.3, 144.4, 301; 128/295, 761, 762; 73/421 R, 425.2 R, 425.4 R

[56] References Cited

U.S. PATENT DOCUMENTS

| | | | |
|---|---|---|---|
| 3,722,503 | 3/1973 | Hovick | 128/295 |
| 4,040,791 | 8/1977 | Kuntz | 128/761 |
| 4,064,760 | 12/1977 | Benjamin | 73/421 R |
| 4,109,530 | 8/1978 | Kim | 128/295 |
| 4,176,412 | 12/1979 | Peterson | 4/144.1 |
| 4,200,112 | 4/1980 | McWhorter | 128/761 |

Primary Examiner—Kyle L. Howell
Assistant Examiner—J. L. Kruter
Attorney, Agent, or Firm—Henry M. Bissell

[57] ABSTRACT

A device for collecting a urine specimen, which is particularly adapted for females, is configured and adapted for use while the user is sitting on a toilet in the normal position for voiding. The device comprises a collector and a specimen container, preferably integrally assembled together. In use the device selectively collects the clean, contaminant-free mid-stream portion of urine in the container. The urine specimen container is releasably secured to the collector at a bleed-off conduit extending from a collection exit in a urine receiving chamber of the collector. This exit is positioned in the chamber above a urine bleed-off exit in the conduit adapted for receiving and discarding the first-voided portion of urine at a controlled rate. Means are provided for directing into the toilet all of the voided urine in excess of that which is retained in the specimen container, including the discarded first-voided portion. A suitable handle extends radially outward from the collector to facilitate holding the device in the preferred attitude for use. In one embodiment, a flow director is included to deflect the first-voided portion from entering the specimen container.

19 Claims, 12 Drawing Figures

URINE SPECIMEN COLLECTING DEVICE

CROSS-REFERENCE TO RELATED APPLICATION

This application is a continuation-in-part of application Ser. No. 31,427, filed Apr. 19, 1979, entitled Urine Specimen Collecting Device.

BACKGROUND OF THE INVENTION

1. Field of the Invention

This invention generally relates to specimen collecting devices and, more particularly, to portable urine specimen collection devices, particularly for use by females.

2. Description of the Prior Art

Urine analysis is such a simple, common and useful diagnostic aid that the taking of a urine specimen is generally included in even the simplest of physical examinations. It is important not only as an indicator or detector of certain physical conditions and diseases, but it is also particularly useful in connection with the treatment of infections related to the urinary tract, which are much more common in females than males. However, the problem of collecting a suitable specimen is considerably more complex when a female patient is involved.

Thus, in the collecting of a urine specimen from a female patient, it is important to take the specimen as a "mid-stream" sample. When a female patient voids in the normal manner, the initial portion is more likely to contain contamination from foreign matter than that portion which follows. This is because the initial portion is expelled with less force and usually is voided as a mere trickle which is likely to trail along the labia and pick up whatever contamination is present in those areas. The mid-stream portion is expelled with the greatest force and is most likely to leave the urethral meatus directly as a stream without contacting the labia or, if it does, the labia will have had most of the contamination washed off by the initial portion.

Some practitioners go to considerable lengths in an effort to obtain an uncontaminated urine sample from a female patient. With the patient in a reclining position, an attendant cleanses the area adjacent the urethral meatus with a suitable solution in an effort to wash off the contamination which is generally present in that area. Even with such precautions, however, contamination may develop in the collected urine sample to a level sufficient to give a false or misleading indication of the bacteria level in the sample. Moreover, taking a sample under such conditions is an extremely awkward and uncomfortable experience for the patient and is fairly costly, since the patient is required to be present in the physician's office or a hospital with a special attendant, usually a nurse, administering the procedure.

What has been needed is some simple but effective, fool-proof device, preferably disposable after a single use, which a patient can use with a minimum of instructions and without assistance, while voiding in the normal manner. The device should have the capability of receiving the entire amount of voided urine, rejecting the initial portion, selecting a portion corresponding to the mid-stream sample and transferring it to a specimen container, and rejecting the remainder of the voided urine by directing it, together with any overflow from the specimen container, into the toilet on which the patent is positioned in the normal attitude.

Although the device set forth in U.S. Pat. No. 4,040,791 which issued on Aug. 9, 1977 to one of the applicants of the present application and is entitled Specimen Collecting Device accomplishes the foregoing objects, such device has been found to be somewhat complicated and expensive to manufacture. For example, it cannot be made in a single high-speed molding operation but must be assembled from a plurality of parts. Moreover, it requires certain close tolerances which demand high quality control. Therefore it is not as simple and inexpensive as one would desire for a disposable device intended for extensive usage. Moreover, it is somewhat difficult to handle and orient while using it. Therefore, it would be desirable to provide an improved device of the same general type which would be as efficient but less expensive, and easier to handle, orient and use.

SUMMARY OF THE INVENTION

The foregoing objects have been achieved by the improved device of the present invention. The device is substantially as set forth in the Abstract above. Not only is it very simple, but it can be rapidly manufactured into a unitary product in a single low-cost molding operation, preferably from inexpensive material, such as plastic, rubber or the like. Moreover, it is highly efficient in isolating and collecting contaminant-free urine. The device is particularly adapted for convenient use by a female patient while she is sitting on a toilet. Thus, she can void urine into the device, and the desired mid-stream sample of urine can be easily and automatically collected. For such purposes the improved device of the invention comprises a collector and a specimen container, the collector comprising a urine-receiving chamber having a urine-receiving opening at its upper end and exit openings at different levels for separating the first-voided portion of urine from the remainder. The first exit is adjacent the lower end of the chamber in a downwardly depending exit conduit. This is for bleeding first-voided urine from the collector at a slow controlled rate into the toilet so that as voiding continues the urine level rises to the second exit which is above the first exit and preferably shielded from the first-voided urine. Thus, the second exit passes clean, contaminant-free mid-stream urine to a detachable urine specimen container positioned to receive urine from the second exit. As voiding continues the urine level in the chamber may rise above the second exit, particularly when the specimen container becomes filled. Any excess urine passes through an overflow passage from the device to the toilet. Thus, the clean mid-stream urine is retained in the specimen container while the rest is discarded. At cessation or diminishing of voiding rate, the excess urine trapped in the chamber exit conduit bleeds out through the first exit until only the urine sample in the specimen container remains.

In one arrangement in accordance with the invention, the collector (apart from the specimen container) is much like a funnel in configuration with a handle extending from the edge thereof. The cone-shaped portion of the funnel corresponds to the collection chamber; the lower central tube of the funnel constitutes the bleed-off conduit and is closed off at the lower end thereof except for an aperture of limited size to control the bleed-off of the first-voided urine at a limited rate. Near the juncture of the collection chamber and the bleed-off conduit is a plurality of apertures or windows, equally spaced about the periphery of the bleed-off conduit, constituting the second exit for communicating with and transferring urine to a specimen container when the specimen container is in place. The specimen container is toroidal in planar cross-section, has both inner and outer walls, and (when mounted together with the collector) surrounds the bleed-off conduit. The specimen container is provided with a flexible lid having a central opening. Mating lip and recess surfaces around the periphery of the specimen container and lid, respectively, provide an effective circumferential seal between lid and container. The portion of the lid surrounding the central opening is spaced upwardly from the upper end of the inner wall of the container, thus defining a circumferential opening which is adjacent the windows at the base of the cone-shaped portion of the collector so as to admit urine therethrough. A mating ring and recess serve to retain the specimen container on the bleed-off conduit, while permitting the collector and container to be separated easily, when desired. Preferably a plurality of upwardly extending shields or dams are located about the base of the collecting chamber in registration with the second exit apertures so as to shield those apertures from urine being voided into the collector until after the first-voided portion fills the bleed-off conduit.

An overflow conduit connecting with the chamber at an overflow exit positioned significantly above the second exit is provided to remove any excess urine from the collector and prevent it from running over its uppermost rim. This overflow exit is also provided with a shield to block urine as voided from passing through the overflow exit.

In a first alternative arrangement of the embodiment described, the overflow exit and overflow conduit connect to the side of the collection chamber in a position radially displaced from the central axis of the device.

In a second alternative arrangement, the overflow conduit is centrally positioned as a standpipe extending upwardly from the closed off exit of the bleed-off conduit. In the latter case, the bleed-off exit opening may be radially displaced and positioned between the wall of the overflow conduit and the inner wall of the bleed-off conduit.

In still another arrangement, the collector has one or more of the exit windows blocked off and is molded with one or more aligned recessed troughs extending downwardly along the bleed-off conduit. This serves in conjunction with the adjacent opening in the specimen container as an overflow passage. Also a flow director or deflector is mounted interiorly of the collector in the region of the exit windows to direct urine initially into the bleed-off conduit from whence it flows into the specimen container. When the specimen container is filled to overflowing, urine flows out of the specimen container at the overflow passage and down the recessed trough(s) and into the toilet. Any further voided urine follows this overflow path out of the device.

In accordance with an aspect of the invention, the flexible lid of the specimen container and the upper edge of the inner wall of the container are configured to mate in sealing relationship when the central portion of the lid is pushed downwardly to engage the inner wall of the container. This serves to complete the closure of the specimen container after the selected urine sample has been collected therein.

To facilitate the sealing operation, the height of the specimen container is made to exceed the length of the bleed-off conduit by approximately ¼ to ½ inch. The collector is provided with a circumferential shoulder surrounding the bleed-off conduit near the juncture of the bleed-off conduit and the collection chamber. This shoulder is provided with a circumferential recess capable of receiving the upper edge of the inner wall of the specimen container when the two are pushed together. When this is done, the central ring portion of the flexible lid is pushed downwardly to engage a circumferential lip surrounding the inner wall of the container, thus retaining the central portion of the lid in the downward position and effectively closing off and sealing the circumferential opening which previously existed between the lid and the upper edge of the inner wall of the container.

By virtue of this arrangement, it is intended that after the patient has used the collector device and left it for the nurse or other medical assistant, the nurse simply pushes downward on the upper circumferential edge of the cone-shaped collecting chamber, thereby driving the lid of the specimen container into sealing relationship with the inner wall of the container. This not only serves to seal the previously existing opening between the lid and the inner wall, but it reinforces the outer circumferential seal between the lid and the outer wall of the container by developing a downward bias on the lid. Thereafter, the nurse simply grasps the specimen container and lid with one hand and removes the collector portion by pulling it upward and away from the specimen container portion. Later, when it is desired to open the specimen container, the lid is simply unsealed by lifting upward relative to the specimen container at the circumferential edge thereof. This serves to release both the inner and outer seals so that the lid can be removed from the container. These various features and aspects of the present invention result in an improved urine specimen collecting device which is extremely effective in collecting the desired contaminant-free midstream portion during use, is readily sealable and separable for retention of the specimen container while the collector proper can be thrown away, is simple, lightweight, cheap to manufacture and easy to use without elaborate instruction.

BRIEF DESCRIPTION OF THE DRAWING

A better understanding of the present invention may be had from a consideration of the following detailed description, taken in conjunction with the accompanying drawing, in which.

DESCRIPTION OF THE PREFERRED EMBODIMENTS

Figures 1, 2, 3:
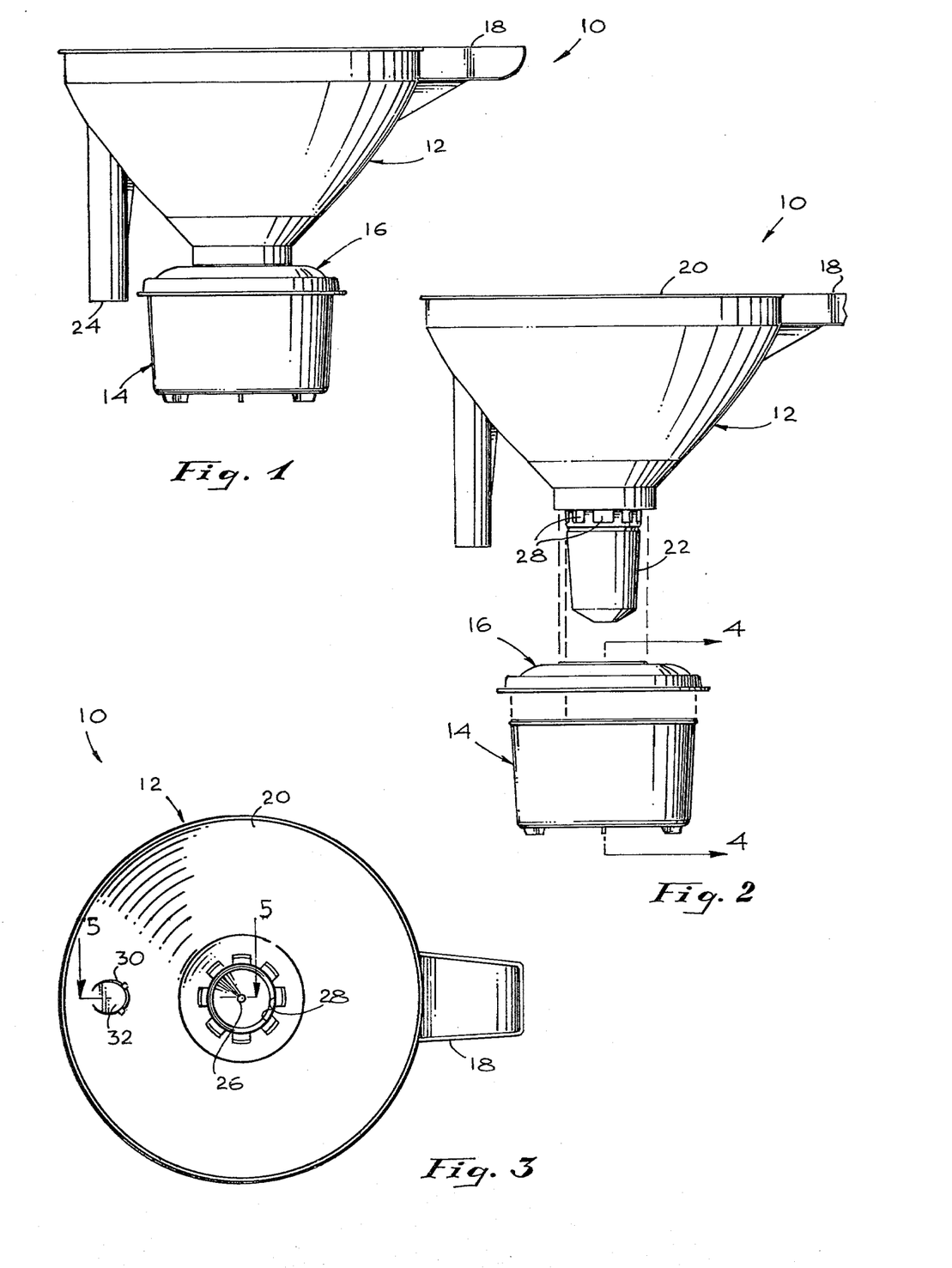
FIG. 1 is an elevational view of one particular arrangement in accordance with the invention.
FIG. 2 is an exploded view of the arrangement shown in FIG. 1.
FIG. 3 is a plan view of the arrangement of FIG. 1.

One preferred embodiment of the present invention is depicted in FIGS. 1-3 of the drawings. As is shown particularly in the exploded view of FIG. 2, the collecting device 10 comprises a collector 12, specimen container 14 and specimen container lid 16.

The collector 12 is a generally funnel-shaped element having a handle 18, a cone-shaped receiving chamber 10, a bleed-off conduit 22 at the lower end of the cone-shaped receiving chamber 20, and an overflow conduit 24 which extends through the sidewall of the receiving chamber 20 and is attached thereto.

The collector 12 is provided with three exits for the release of urine therefrom. The first exit is a bleed-off exit 26 comprising a small hole at the bottom of the bleed-off conduit 22, the bottom of which is otherwise closed off and thereby constitutes a pocket or recess for receiving the first-voided urine from the chamber 20. The second exit comprises a plurality of apertures or windows 28 near the bottom of the cone-shaped portion of the chamber 20. As will be shown in detail hereinbelow, these windows 28 communicate with the interior of the specimen container 14 when the constituent elements are assembled in the configuration shown in FIG. 1. A third exit 30 is located in the side of the chamber 20 above the second exit 28 and communicates with the interior of the overflow conduit 24. The overflow exit 30 is provided with a shield 32 to block the overflow of urine via that exit 30 until the urine level in the collector 12 rises to the overflow exit 30.

Figures 4, 5:
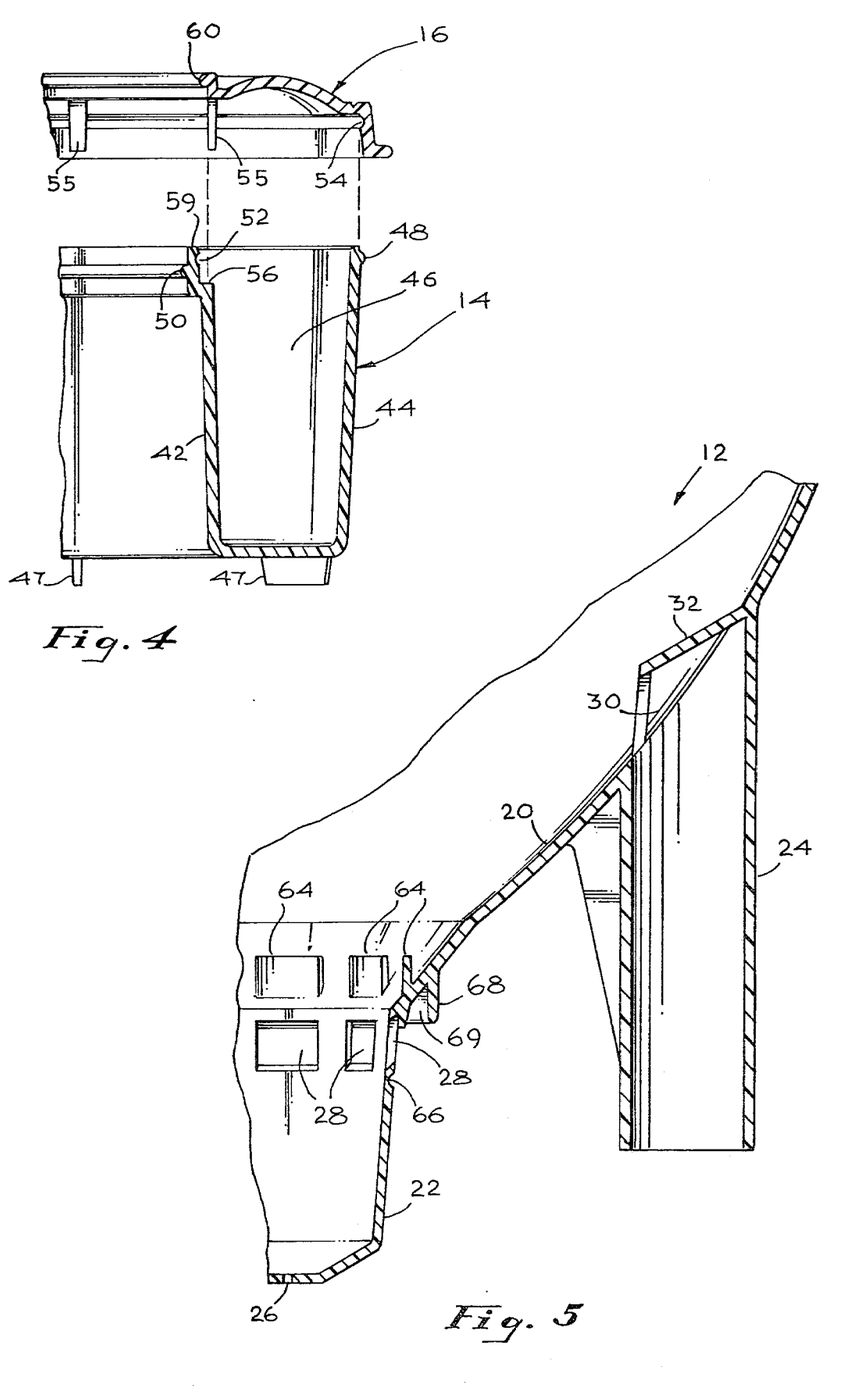
FIG. 4 is a quarter-sectional view of a portion of the arrangement depicted in FIG. 2, taken along the line 4—4 thereof.
FIG. 5 is a quarter-sectional view of a portion of the arrangement of FIG. 1, taken along the line 5—5 of FIG. 3.

As seen in FIG. 4, which is a quarter-sectional view of a portion of the arrangement of FIG. 2, taken along the line 4—4 and looking in the direction of the arrows, the specimen container 14 is somewhat toroidal in form, having an upstanding hollow center section surrounded by an inner cylindrical wall 42 and an outer cylindrical wall 44. The storage space for urine collected in the container 14 is between the inner and outer walls 42, 44. This space 46 is open at the top of the container 14. Legs 47 are mounted at the base of the container 14.

Near the top of the outer cylindrical wall 44 is an outwardly protruding lip or rim 48 which extends circumferentially about the specimen container 14. A similar protruding lip or rim 50 projects radially inwardly from the inner wall 42 and extends circumferentially about the hollow space defined by the wall 42. Near the top of the wall 42 in the side facing the space 46 is a recess or slot 52 which extends circumferentially about the specimen container inner wall 42.

The lid 16 is provided with an inner circumferential recess 54 which serves to mate with the rim 48 of the container 14 when the lid 16 is mounted on the container 14, thus retaining the lid thereon in sealing relationship about the outer edge of the container 14. The lid 16 is provided with a plurality of downwardly depending, projecting stop pins 55 which, when the lid 16 is first placed on the container 14, bear against a ledge 56 on the inner wall 42 of the container 14 and maintain a space between the ring 58 about the central opening of the lid 16 and the upper edge 59 of the inner wall 42 of the container 14. These stop pins 55 are flexible, as is the lid 16, so that upon the application of downward force sufficient to bend the pins 55, they give way and permit an inwardly projecting rim 60 of the lid 16 to move downwardly into engagement with the circumferential recess 52, thus establishing a seal between the inner rim 60 of the lid 16 and the upper end of the inner wall 42 of the container 14. When mounted in such fashion, the storage space 46 for the urine which is collected in the container 14 is completely sealed—at the outer edge by the seal between the outer rim 48 and the recess 54, and at the inner edge by the seal between the inner rim 60 and the recess 52.

Referring now to FIG. 5, a sectional view taken along the line 5—5 of FIG. 3 and looking in the direction of the arrows, certain structural details of the collecting device of our invention are shown therein. FIG. 5 shows the sidewall of the receiving chamber 20 in the region of the overflow conduit 24 and the collecting exit comprising the windows or apertures 28. The overflow exit 30 may be seen extending through the sidewall of the receiving chamber 20 and communicating with the overflow conduit 24. As shown, the exit 30 is protected by the shield 32 to minimize the splashing of urine through the exit 30. Shields or barriers 64 serving as tiny dams are mounted respectively above the windows 28 to interfere with the flow of the first-voided urine through the windows 28. These barriers 64 channel the urine through the passages between adjacent barriers 64, thus diverting the urine from the windows 28 until the urine rises in the bleed-off conduit 22 to the level of the windows 28.

The sidewall of the bleed-off conduit 22 is provided with a circumferential recess 66 positioned just below the windows 28. This serves to receive the inner rim 50 of the container 14, thus retaining the container 14 in sealing relationship to the collector 12 when the two are affixed together. Of course, the lid 16 will be positioned between the collector 12 and container 14 when mounted in this fashion (see FIG. 6).

The collector 12 is provided with a downwardly depending, circumferential skirt or lip 68 which defines, with the wall of the bleed-off conduit 22, a circumferential recess 69.

Figure 6:
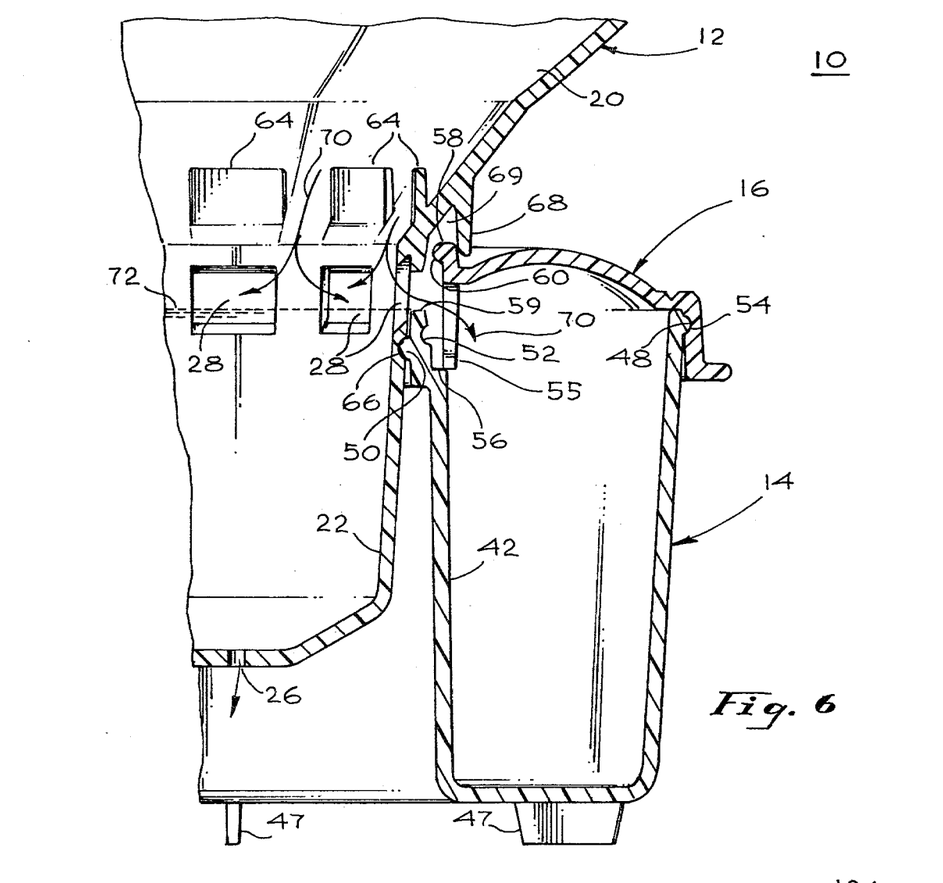
FIG. 6 is a sectional view similar to FIG. 5, showing the assembly of the various elements making up the arrangement of the invention.

FIG. 6 is a sectional view similar to that of FIG. 5 but showing the container 14, lid 16 and collector 12 assembled together as prepared for shipment and for operative use in selectively collecting a mid-stream urine specimen. The lid 16 is shown in place on the container 14 with the outer periphery of the lid sealed to the container 14 by virtue of the mating of the rim 48 in the circumferential recess 54. Similarly, the inner wall of the specimen container 14 is sealably engaged to the bleed-off conduit 22, and thereby retained thereon, by the mating relationship of the inner rim 50 in the circumferential recess 66. The central circumferential ring 58 of the cover 16 surrounding the central opening thereof is partially within the recess 69 and bearing against the skirt 68. A stop pin 55 is shown bearing against the ledge 56, thus maintaining the space between the upper edge 59 of the wall 42 and the lid 16. This space is adjacent the windows 28 and extends circumferentially about the assembly, interrupted only by the spaced-apart pins 55.

When the collector device is used by a patient, urine is voided into the receiving chamber 20 of the collector 12. The first-voided urine flows down into the bleed-off conduit 22 and begins bleeding out the bleed-out exit opening 26; if the urine initially drops onto the wall of the receiving chamber 20, it flows down the wall and in the channels between the barriers or dams 64, as indicated by the arrows 70. When the urine level rises to the windows 28, as indicated by the line 72, urine then begins flowing through the windows 28 and through the entrance space between the lid 16 and the inner wall 42 of the specimen container 14, as further indicated by the arrows 70. As voiding continues, the mid-stream portion of the voiding is directed in the manner described into the specimen container 14. As the specimen container 14 fills with urine, the air which was initially in the empty container 14 is permitted to escape out the same entrance space and the windows 28. Further voiding after the specimen container 14 is full backs up into the receiving chamber 20 until the level of the overflow exit 30 (FIG. 5) is reached, after which the overflow urine runs out the overflow conduit 24. When voiding is terminated, the urine remaining in the collector bleeds off through the bleed-off conduit 22 and exit 26, until the collector 12 is emptied.

At this point, the patient will normally deliver the collector and specimen container with the specimen contained therein to the nurse or other medical assistant who thereafter places the device 10 on a counter, table or other horizontal surface and bears down on the upper edge of the collector 12. This causes the skirt 68 to bear down against the adjacent surface of the lid 16 as the ring 59 of the lid moves further into the recess 69 and causes the semi-flexible pins 55 to bend and slip off the ledge 56. Further downward movement of the collector 12 relative to the specimen container 14 causes the inner rim 60 of the lid 16 to move downwardly into engagement with the circumferential recess 52, effecting the seal between the rim 60 and the recess 52 and thus preventing any escape of the specimen collected within the container 14. The collector 12 is then pulled upwardly, relative to the lid 16 and container 14, releasing the retention of the container 14 on the bleed-off conduit 22 at the recess 66 and separating the collector from the specimen container. The collector 12 is then discarded and the specimen container retained for processing of the collected specimen.

Figures 7, 8:
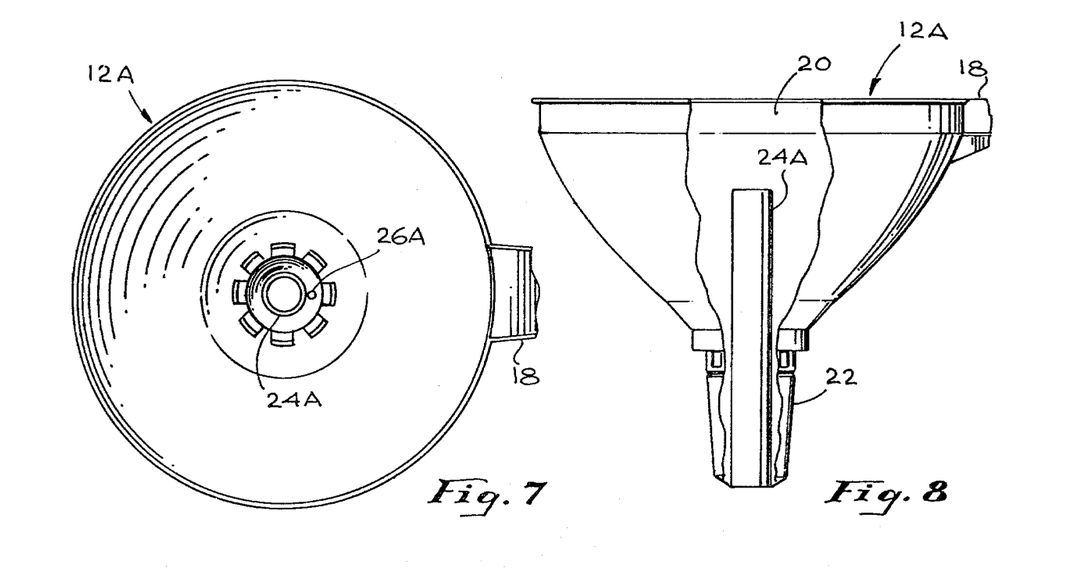
FIG. 7 is a plan view of an alternative embodiment of the invention.
FIG. 8 is an elevational view, partially broken away, of a portion of the alternative embodiment of FIG. 7.
Figure 9:
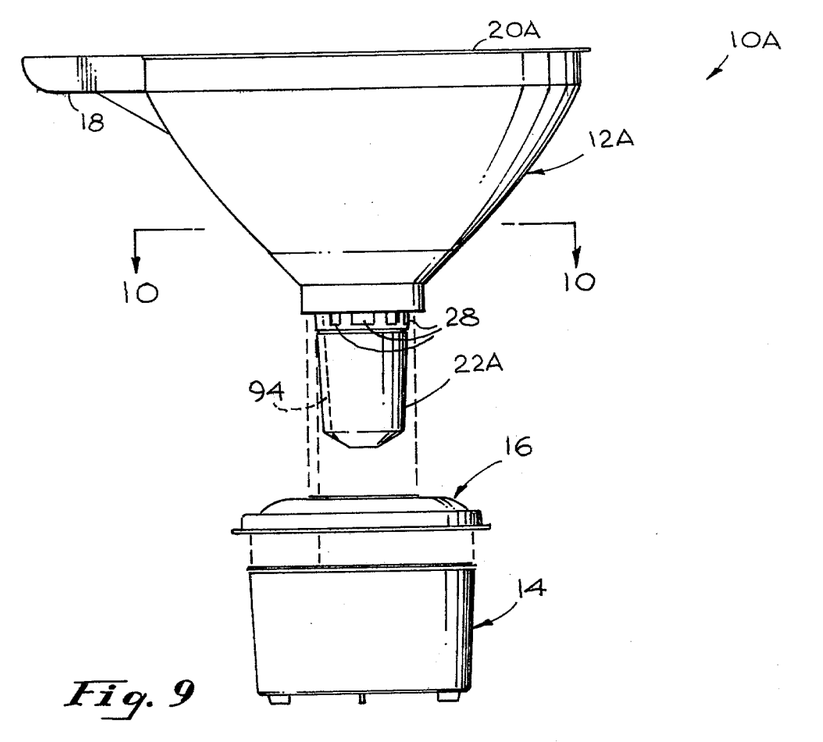
FIG. 9 is an exploded elevational view of still another arrangement in accordance with the invention.

An alternative embodiment of the invention is shown in FIGS. 7 and 8. In this embodiment, the elements of the collecting device 1 are the same as shown in FIGS. 1-6, except that the overflow conduit 24A is centrally located within the bleed-off conduit 22. The bleed-off exit opening 26A is shown at the bottom of the bleed-off conduit 22 (see FIG. 7) but located between the wall of the overflow conduit 24A and the inner wall of the bleed-off conduit 22. The bottom of the overflow conduit 24A is of course open to permit the escape of urine overflowing through the conduit 24A. Utilization of this alternative embodiment of the collector 12A, when assembled in combination with the specimen container 14 and the lid 16, is the same as has been described for the use of the embodiments of FIGS. 1-6.

The device depicted in FIGS. 9-12 is a variant of the arrangement shown in FIGS. 1-6. Where like elements are included, the same reference numerals have been employed. As shown particularly in FIGS. 9 and 10, the device 10A includes a collector 12A and an integral specimen container 14 and associated lid 16. The notable difference is the lack of an overflow conduit per se such as the conduit 24 shown in FIG. 1.

The collector 12A has a receiving chamber 20 in the upper portion of the generally funnel-shaped configuration opening into a downwardly depending bleed-off conduit 22A, near the bottom of which is a first or drain exit 26 for draining urine from the collector. A second or transfer exit is provided by the window openings 28 which are spaced about the periphery of the upper portion of the exit or bleed-off conduit 22A except on the side in line with the handle 18. At this point, the periphery of the collector 12A is closed and, further, the collector is molded with a recessed trough 94 (see FIG. 10) extending downwardly along the bleed-off conduit 22A. This trough 94 serves to provide an overflow passage for any urine tending to overflow the specimen container 14, thus permitting such excess urine to flow downwardly and outwardly from the urine collecting device 10A and directly into the toilet.

Figure 12:
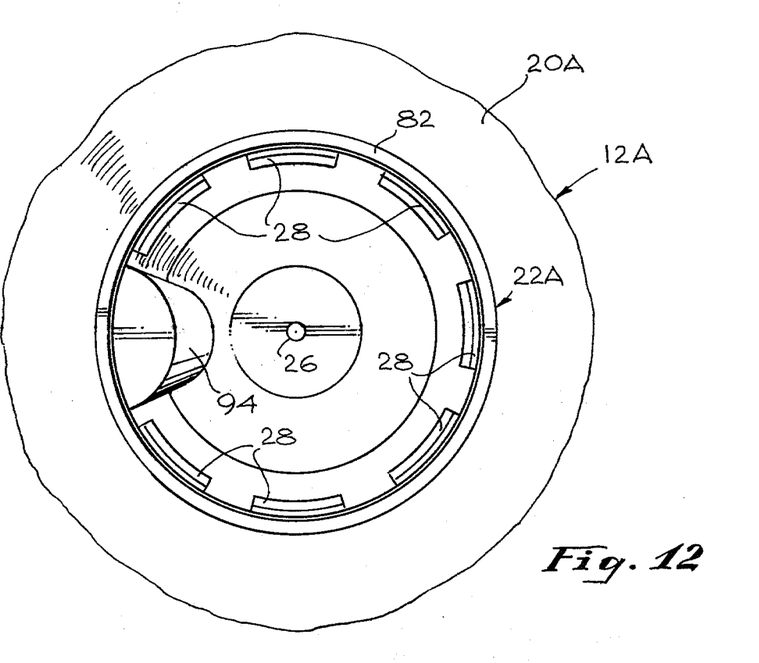
FIG. 12 is an upper plan view of the portion of the collector shown in FIG. 10.

To provide more effective control of the flow of urine being voided into the collecting device 10A, a diverter or deflector insert 80 may be mounted in the device at the bottom of the receiving chamber 20. This deflector 80 is configured to adapt to the interior shape of the collector 12A, i.e. the diverter 80 is also generally funnel-shaped, and is provided with an outer lip 88 to collect urine flowing down the walls of the receiving chamber 20 and direct it into the bleed-off conduit 22A through the lower opening 90 of the diverter 80. The interior of the collector 12A is provided with a circumferential wall 82 projecting upwardly by a sufficient distance to engage and retain the diverter 80. This wall is provided with an inwardly projecting ring 84 adapted to mate with a corresponding circumferential recess 86 in the diverter 80. Thus, the diverter 80 is retained in the position shown in FIG. 10 after it is simply snapped in position by downward pressure on the diverter 80 during assembly. The portion of the collector 12A shown in FIG. 12 is as it appears prior to insertion of the diverter 80. The diverter 80, in use, serves to prevent urine from flowing out the windows 28 and into the specimen container 14 until after the urine has entered the bleed-off conduit 22A, thus insuring that none of the unwanted, first-voided urine can inadvertently enter the specimen container.

In use, the collecting device 10A is held by the female subject, grasped by the handle 18 between thumb and forefinger and held in a proper position for receiving voided urine while the subject is sitting on a toilet. Use in the normal attitude thus orients the device at an angle which locates that portion of the opening between the portion 50 of the specimen container 14 and the inner ring portion 58 of the lid 16 which is adjacent the trough 94 somewhat higher than the remainder of the opening. This thus provides for the escape of air which might otherwise be entrapped within the specimen container 14 and prevent it from being adequately filled with the desired specimen. Furthermore, this portion, in conjunction with the recessed trough 94, establishes an overflow passage, permitting excess urine to flow out of the device, once the specimen container 14 is substantially filled. Thus, any excess urine is rapidly directed out of the device and into the toilet via this overflow passage including the trough 94 until voiding is terminated. At that point, the subject need only wait a very brief interval until the small amount of urine in the bleed-off conduit 22A drains out through the drain hole 26 before she can turn the collecting device 10A with specimen contained therein over to the nurse or other attendant.

Figure 10:
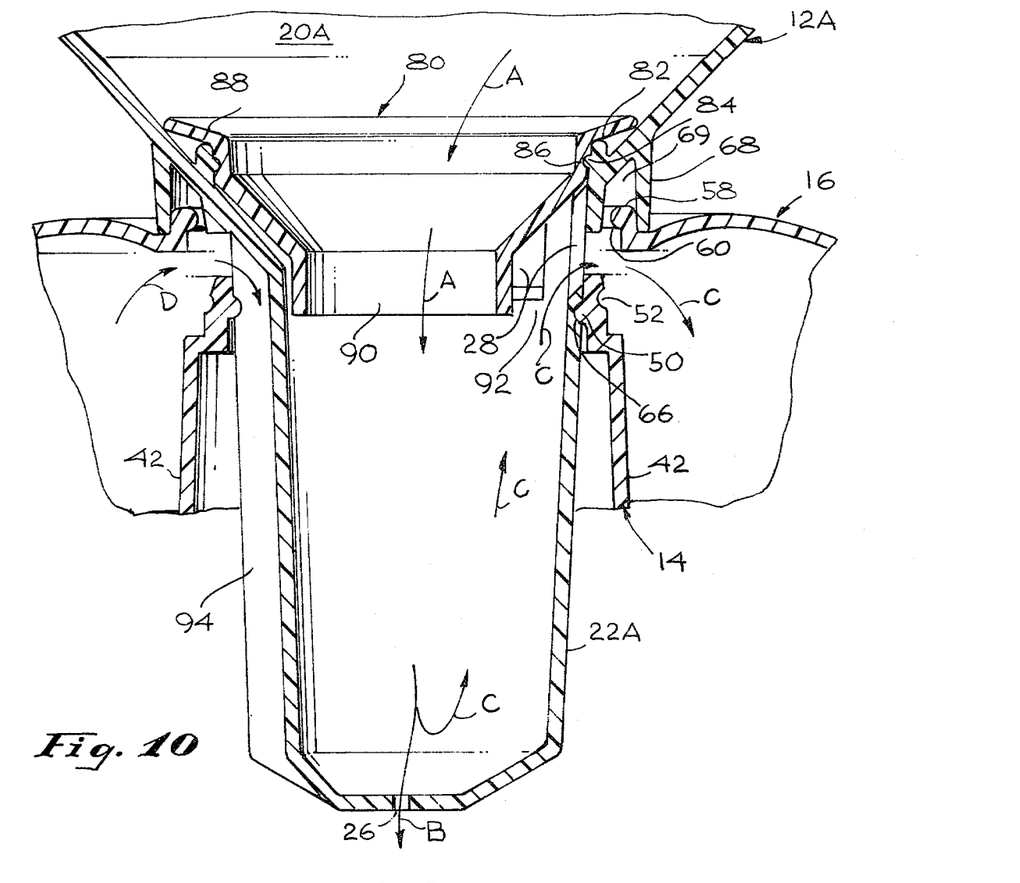
FIG. 10 is a sectional view of a portion of the arrangement depicted in FIG. 9 taken along the plane of the drawing and looking upward from the drawing plane.
Figure 11:
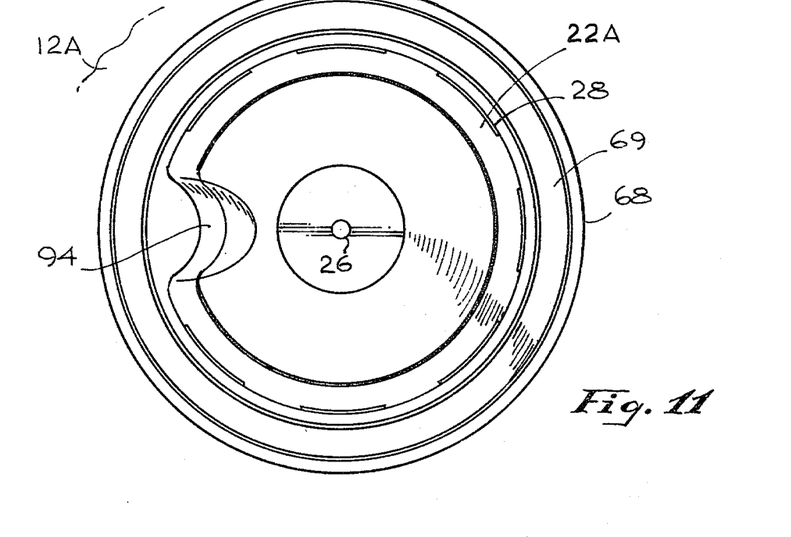
FIG. 11 is a bottom view of the portion of the collector element shown in FIG. 10.

As particularly shown in FIG. 10, urine received into the collector 12A flows downwardly in the direction of the arrows A into the bleed-off conduit 22A. Thereafter, the flow divides as shown by arrows B and C. A portion of the urine flows out through the drain 26 (arrow B) while the remaining portion is directed upwardly (arrows C) to fill the bleed-off conduit 22A and ultimately begin overflowing into the region 92 and entering the specimen container 14. When the level of urine in the specimen container 14 reaches the overflow passage on the left-hand side of FIG. 10, it flows outwardly (arrows D) from the specimen container 14 and downwardly through the space between the bleed-off conduit 22A and the wall 42 of the specimen container 14 via the trough 94. When voiding is finished, any urine remaining in the collector 12A drains through the drain opening 26 until the collector per se is empty. The only urine remaining is in the specimen container 14. Thereafter, the collecting device 10A is processed as previously described to seal the lid 16 on the container 14 and remove the specimen and container from the collector, which is discarded.

Arrangements in accordance with the present invention are particularly effective in the collection of the preferred mid-stream portion of voided urine for transfer to and retention in a specimen container. The collecting device is simple to use without the need for any special instructions and its utilization is virtually foolproof. After the device is used by the patient, sealing of the specimen container and lid with removal of the collector from the specimen container is virtually automatic by any personnel without the need for any special training. The various components of the device are preferably molded from high density polyethylene with a wall thickness of 0.035 inches, although other materials may be used, as appropriate. The molding operation is simple and the cost of the manufactured product is low so that the device is readily disposable after a single use. During manufacture the components of the device are readily sterilized so that the device can simply be unwrapped, used and thrown away without the necessity of on-site sterilization procedures.

Although there have been described above specific arrangements of an improved urine specimen collecting device in accordance with the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A urine specimen collecting device for selectively collecting a mid-stream portion of voided urine, the device comprising in combination:
    an integral collector and specimen container, the collector having a first drain exit and a second transfer exit for different portions of the voided urine, the first exit being positioned near the bottom of the collector for bleeding off the first-voided urine, the second exit being positioned above the first exit for transferring urine following the first-voided urine to the specimen container;
    the collector including a bleed-off conduit extending between the first and second exits;
    the specimen container being toroidally-shaped and configured for releasable mounting on the bleed-off conduit in a position surrounding said conduit for receiving urine flowing through the second exit;
    a flexible lid sealingly mounted on the specimen container about the periphery thereof and having a central ring opening spaced from the container to define an opening adjacent the second exit for transferring a specimen of urine into the container; and
    overflow means coupled to the specimen container for transferring excess urine from the device.

2. The device of claim 1 wherein the collector is generally funnel-shaped with a cone-shaped portion constituting a receiving chamber and a downwardly depending tubular portion connected to the receiving chamber and constituting the bleed-off conduit, the bleed-off conduit being closed off at its lower end except for a bleed-off exit of limited opening size to limit the rate of urine flow therethrough.

3. The device of claim 2 wherein the second exit comprises a plurality of circumferentially spaced windows extending about the collector in the vicinity of the juncture between the bleed-off conduit and the receiving chamber.

4. The device of claim 3 further including means for diverting urine from the receiving chamber away from said windows until the bleed-off conduit is filled with the first-voided portion.

5. The device of claim 4 wherein said means comprise a generally funnel-shaped diverter configured to be inserted in retained juxtaposition in the lower portion of the receiving chamber and extending downwardly into the bleed-off conduit to overlap said windows and divert urine therefrom.

6. The device of claim 5 wherein said means further comprises a raised circumferential wall about the base of the receiving chamber and including retaining means for mating with corresponding means about the periphery of the diverter.

7. The device of claim 1 wherein the specimen container includes separate inner and outer circumferential walls defining a specimen storage space closed at the bottom and open at the top, the inner wall defining a hollow open space and having an inwardly directed, circumferential rim near the upper end of the inner wall for engaging a mating circumferential recess on the bleed-off conduit of the collector.

8. The device of claim 7 wherein the outer wall includes an outwardly extending circumferential rim near the upper end of the outer wall for engaging a mating circumferential recess in the inner surface of the lid about the periphery thereof.

9. The device of claim 8 wherein the inner wall is provided with a circumferential recess near the upper end of the wall for sealingly engaging a mating portion of the container lid.

10. The device of claim 9 wherein the lid is flexible and comprises a downwardly depending outer wall having a circumferential recess extending about the inner surface thereof for mating in sealing relationship with the corresponding circumferential rim of the container.

11. The device of claim 10 wherein the lid further comprises an inner circumferential ring defining a central opening, said ring having an inwardly projecting circumferential rim for mating in sealing relationship with a corresponding circumferential recess extending about the inner wall of the container.

12. The device of claim 10 wherein the collector further comprises a circumferentially extending, downwardly directed skirt configured to bear against the central portion of the lid upon the application of force upon the collector in the direction toward the container to deflect the inner portion of the lid into sealing engagement with the inner wall of the container.

13. The device of claim 3 further including a solid wall portion extending between a pair of adjacent windows in the vicinity of the opening between the lid and container, the wall portion being recessed radially inwardly, the recessed portion extending downwardly along the bleed-off conduit to define, with said opening, an overflow passage for excess urine.

14. The device of claim 13 further comprising an outwardly directed, radially extending handle attached to the outer periphery of the collector adjacent the upper rim thereof, said handle and collector being symmetrically configured to facilitate use by either right-handed or left-handed users with equal convenience.

15. The device of claim 14 wherein the recessed wall portion is selectively located in alignment with and on the same side of the device as the handle.

16. The device of claim 1 further comprising means extending along the outside of the bleed-off conduit for defining an overflow passage for excess urine overflowing the specimen container, said overflow means serving to direct said excess urine out of the device.

17. The device of claim 16 wherein said overflow means also provides means for releasing entrapped air from the specimen container.

18. The device of claim 1 further comprising support members appended to the bottom of the specimen container and wherein the bleed-off conduit of the collector terminates a predetermined distance above the support means sufficient to permit downward motion of the collector to the position at which the central ring opening of the lid engages the inner wall of the container.

19. The device of claim 1 wherein the specimen container includes separate inner and outer circumferential walls defining a specimen storage space closed at the bottom and open at the top, the inner wall defining a hollow open space for receiving a portion of the bleed-off conduit therein, and mating surface engaging means for selectively sealing the outer peripheral edge of the lid to the outer wall of the container and the central ring opening of the lid to the inner wall of the container.

* * * * *